United States Patent [19]
Bidoia

[11] Patent Number: 5,129,888
[45] Date of Patent: Jul. 14, 1992

[54] SUPPORT PARTICULARLY FOR INJECTIONS OR SAMPLINGS

[76] Inventor: Gianfranco Bidoia, Via Bressanone 3/A, 35100 Padua, Italy

[21] Appl. No.: 466,454
[22] PCT Filed: Sep. 21, 1989
[86] PCT No.: PCT/EP89/01101
§ 371 Date: May 24, 1990
§ 102(e) Date: May 24, 1990
[87] PCT Pub. No.: WO90/03197
PCT Pub. Date: Apr. 5, 1990

[30] Foreign Application Priority Data

Sep. 28, 1988 [IT] Italy .................. 41680 A/88

[51] Int. Cl.⁵ .................................. A61M 5/00
[52] U.S. Cl. ........................... 604/240; 604/187; 604/110; 604/232; 128/763
[58] Field of Search ........... 604/110, 239–243, 604/232, 187, 218; 128/763, 919

[56] References Cited

U.S. PATENT DOCUMENTS

| | | | |
|---|---|---|---|
| Re. 16,836 | 12/1927 | Cook | 604/241 X |
| 2,720,880 | 10/1955 | Whitaker et al. | 604/232 |
| 2,737,949 | 3/1956 | Brown | 604/243 X |
| 3,320,954 | 5/1967 | Cowley | 604/110 |
| 3,326,206 | 6/1967 | Barr et al. | 604/239 X |
| 3,410,267 | 12/1968 | Nöjd | 604/232 |
| 3,491,757 | 1/1970 | Arce | 604/242 |
| 3,556,099 | 1/1971 | Knight | 604/232 |
| 3,976,069 | 8/1976 | Ong | 604/232 X |
| 4,027,669 | 6/1977 | Johnston et al. | 604/110 |
| 4,540,405 | 9/1985 | Miller et al. | 604/232 |
| 4,731,059 | 3/1988 | Wanderer et al. | 604/192 |
| 4,844,089 | 7/1989 | Roberti | 128/764 |
| 4,950,253 | 8/1990 | Jacobs | 604/218 |
| 4,976,925 | 12/1990 | Porcher et al. | 422/100 |
| 4,984,580 | 1/1991 | Wanamaker | 128/763 |
| 4,993,426 | 2/1991 | Spencer | 128/763 |

FOREIGN PATENT DOCUMENTS

| | | | |
|---|---|---|---|
| 0660402 | 4/1963 | Canada | 604/242 |
| 0608043 | 4/1926 | France | 604/243 |
| 641763 | 8/1928 | France | 604/240 |
| 1098722 | 8/1955 | France | 604/240 |
| 292032 | 6/1928 | United Kingdom | 604/242 |
| 0802351 | 10/1958 | United Kingdom | 604/240 |
| 1191634 | 5/1970 | United Kingdom | 604/424 |
| 9011789 | 10/1990 | World Int. Prop. O. | 604/242 |

*Primary Examiner*—C. Fred Rosenbaum
*Assistant Examiner*—Mark O. Polutta
*Attorney, Agent, or Firm*—Guido Modiano; Albert Josif

[57] ABSTRACT

The support according to the invention comprises a preferably tubular hollow body which is provided, at one end, with a fixed or removable bottom from which a needle coupling element protrudes. The coupling element is provided with a breaking portion which facilitates its separation from the bottom. In this manner it is therefore possible to immediately and easily separate the needle which is coupled thereto from the support after use. The used needles and supports thus separated can be collected in appropriate containers.

8 Claims, 1 Drawing Sheet

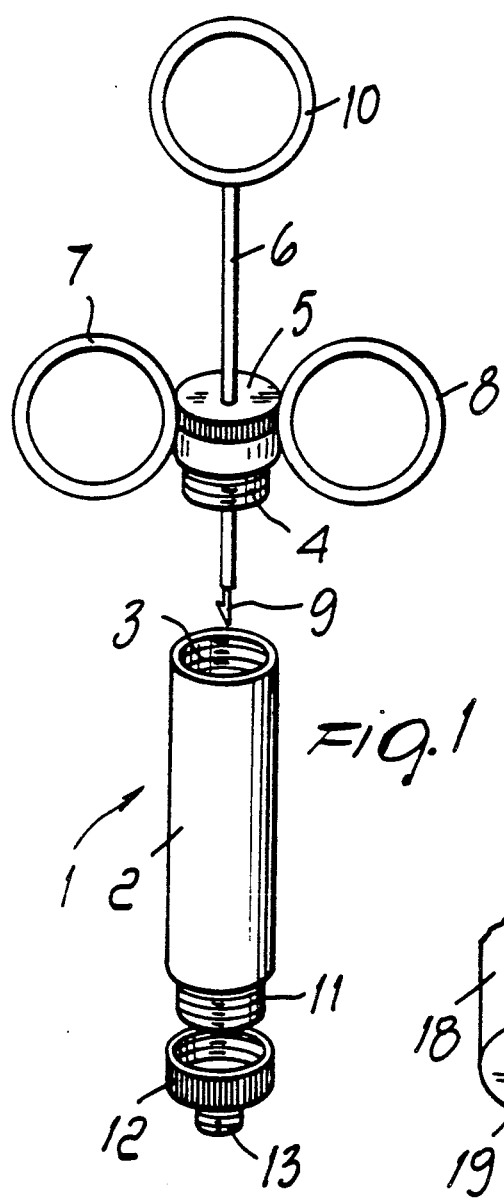
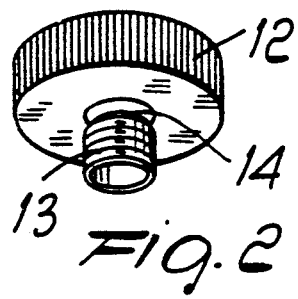
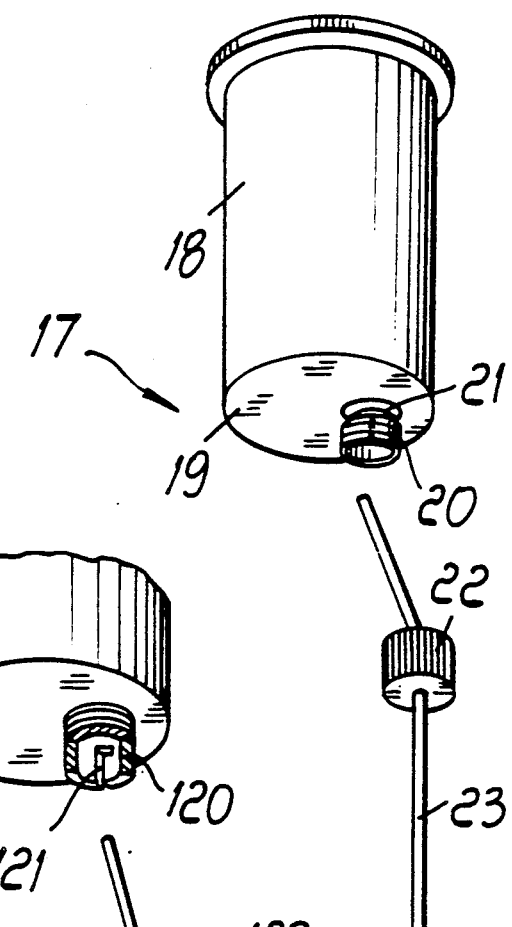
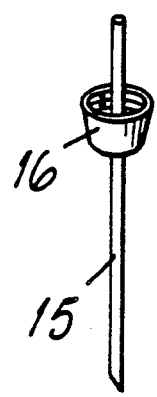

SUPPORT PARTICULARLY FOR INJECTIONS OR SAMPLINGS

BACKGROUND OF THE INVENTION

The present invention relates to a support particularly for injections or samplings.

Hollow supports made of steel, to one end whereof metallic needles are coupled, are commonly used in the medical field; besides the normal outer pointed portion, said needles comprise a portion which is arranged inside the supports and is provided with a second point.

Ampoules filled with pre-dosed anaesthetic are arranged in said supports.

Said ampoules are provided, at one end, with a membrane lid made of rubber-like material, into which the second point of the needle penetrates; a plunger is slidable in said ampoules from the other end and injects the anaesthetic by being pushed by a rod rigidly coupled to said support.

Syringes constituted by a cylindrical body made of plastic material and/or metal, to which one of said two-pointed needles is screwed, are also commonly used.

Containers shaped complementarily to the internal surfaces and in which a vacuum has been produced are insertable in said cylindrical body.

Said containers, like the above-mentioned ampoules, are provided with a membrane lid into which the second point of the needle penetrates, allowing the liquid to be drawn inside.

In these and other cases, the coupling between the support and the needle is obtained with a stable screw coupling or with systems designed so that the parts are not separable after use without at least some effort.

However, in this manner, during these separation operations the user is exposed to the danger of accidental lesions or even of infections arising from the possible contamination of the needle with the blood of a patient.

SUMMARY OF THE INVENTION

The aim of the present invention is to provide a support, particularly for injections or samplings, which allows one to avoid the manual handling of the ampoule after its use.

Within the scope of the above-described aim, a primary object is to provide a support for injections or samplings which can be used only once, the structure and the needle which has separated therefrom after use being collectable in suitable containers.

Another important object is to provide a support for injections or samplings in which the needle can be separated without the operator making contact therewith.

Another important object is to provide a support by means of which the needle is separated after use in an easy and rapid manner and in conditions of maximum safety.

Still another object is to provide a support the constructive principles whereof can be effectively applied to all kinds of devices for injections or samplings.

Not least object is to provide a support for injections or samplings which has a low cost.

This aim, these objects and others which will become apparent hereinafter are achieved by a support particularly for injections or samplings which comprises a hollow body provided, at one end, with a fixed or removable bottom from which a needle coupling element protrudes, characterized in that it has at least one breaking portion which facilitates the separation of said needle coupling element from said bottom.

BRIEF DESCRIPTION OF THE DRAWINGS

Further characteristics and advantages of the invention will become apparent from the detailed description of some embodiments thereof, illustrated only by way of non-limitative example in the accompanying drawings, wherein:

FIG. 1 is an exploded perspective view of a dental syringe according to the invention;

FIG. 2 is an enlarged perspective detail view of the bottom of the dental syringe of FIG. 1;

FIG. 3 is an exploded perspective view of a container used for samplings, provided with an axially offset needle coupling element with screw coupling;

FIG. 4 is a further embodiment of the container of FIG. 3, with bayonet-like needle coupling.

DESCRIPTION OF THE PREFERRED EMBODIMENTS

With reference to the above-described figures, a dental syringe according to the invention is generally indicated by the reference numeral 1 and comprises a tubular support 2 which is provided, at one end, with an internal thread 3 which allows its coupling to a complementarily threaded end 4 of a lid 5 to which a rod 6 is slidably axially coupled.

Said lid 5 is provided with two diametrically opposite rings, respectively 7 and 8, while said rod is provided with a hook-like point 9 at the end arranged inside the support 2 and with a ring 10 at the opposite end.

Said tubular support 2 is provided, at the end arranged opposite to said lid 5, with an outer thread 11 on which a complementarily threaded bottom 12 can be screwed; an externally threaded tubular element 13 extends axially from said bottom and is provided, proximate to its base, with a circumferential breaking portion 14 which has, as seen in FIG. 2, a reduced thickness with respect to the remaining thickness of the tubular element 13.

A two-pointed needle 15 is provided, in a median portion, with an internally threaded bush 16 can be screwed onto said element 13.

An ampoule containing anaesthetic liquid can be inserted in said dental syringe 1 and is provided with a perforatable membrane at the end corresponding to said bottom 12 and with a plunger at the opposite end; said plunger is slidable by virtue of the action of said rod 6.

Still according to the invention, a structure suitable to be used for samplings is generally indicated by the reference numeral 17 and comprises a tubular vial-holder body which is monolithic with a bottom 19 from which an externally threaded tubular element 20 protrudes in an axially offset position; said element 20 is provided, proximate to its base, with a circumferential breaking portion 21.

A complementarily threaded bush 22 can be screwed onto said element 20; said bush 22 is provided in a median position on a two-pointed needle 23, and the end of said needle which can be inserted in said tubular body 18 is bent so that the point can be central after coupling.

In a further embodiment of the support for samplings, the tubular element which protrudes from the bottom 19 and is now indicated by 120 is provided with guiding recesses 121 on its inner surface; pins 122 are engageable bayonet-like in said recesses 121 and protrude externally from a cylindrical element 123 which is provided in a median position on a two-pointed needle which is now indicated by 124 and is provided, like the previous one, with a bent end.

Vials, shaped complementarily to the internal surfaces and in which a vacuum has been provided beforehand, are insertable in the tubular body 18.

Said vials have a membrane lid made of rubber-like material into which the inner point of the needle penetrates, allowing liquid to be drawn.

In all the embodiments of the invention, the needle can be easily removed from the support after use simply by acting thereon so as to break, at the circumferential breaking portion, the coupling element which protrudes from the bottom.

This action can be obtained by completely inserting the needle in holes provided in appropriate containers and by then exerting leverage on the support.

The supports separated from the needles can be collected in other containers and disposed of.

From what has been described and illustrated above it is thus evident that the invention has brilliantly eliminated the disadvantages of the known art, achieving the intended aim and objects.

All the dangers arising from the possible accidental contact of the needles after use have been in fact eliminated, consequently eliminating the risk that the operators may contract infections.

The invention thus conceived is susceptible to numerous modifications and variations, all of which are within the scope of the inventive concept.

All the details may furthermore be replaced with other technically equivalent elements.

In practice, the materials employed, as well as the dimensions, may be any according to the requirements.

I claim:

1. Syringe device, comprising a hollow tubular vial-holder body and a needle, said hollow tubular body being provided, at one end, with a bottom sealingly attached thereto, said bottom having connected thereto a needle coupling tubular element protruding from said bottom along an axial direction with respect to said tubular body, said needle coupling tubular element comprising means to sealingly couple to a complementary coupling element provided in a median position along the length of said needle, one end of said needle being internal to said hollow body, said needle coupling tubular element comprising at least one breaking portion, said at least one breaking portion being provided circumferentially around said needle coupling tubular element and having a reduced thickness with respect to the remaining thickness of said needle coupling tubular element which thereby facilitates the separation of said needle coupling tubular element from said bottom after use of the device, said hollow tubular body being provided at its opposite end to said bottom with an internal threading on its internal wall, said syringe device further comprising a lid having an externally threaded lower end, said lower end of said lid being screwably connected to said opposite end of said hollow tubular body, said lid securing a vial inside said hollow tubular body.

2. Device according to claim 1, wherein said needle coupling element protrudes from said bottom along said axial direction and radially offset from the axis of said hollow tubular body, said needle internal to said hollow body being oriented at an angle to the axis of said hollow body with said end of said needle internal to said hollow body lying at a point substantially along the axis of said hollow body.

3. Device according to claim 1, wherein said at least one breaking portion extends on at least a portion of the outer surface of said needle coupling element.

4. Device according to claim 1, wherein said at least one breaking portion extends on at least a portion of the inner surface of said needle coupling element.

5. Device according to claim 1, wherein said at least one breaking portion is provided in a position which is circumferentially external to said needle coupling element at a point where said needle coupling element is connected to said bottom of said hollow body.

6. Device according to claim 1, wherein said needle coupling tubular element and said complementary coupling element are threaded coupling elements.

7. Device according to claim 1, wherein said needle coupling tubular element and said complementary coupling element are bayonet-like coupling elements.

8. Device according to claim 1, wherein said lid has two diametrically opposite grip elements, a rod being slidably coupled to said lid and passing through said lid along an axial direction with respect to said tubular body, said rod having a grip element at one end external to the hollow body and a hook-like point at the end internal to the hollow body.

* * * * *